United States Patent
Star et al.

(10) Patent No.: US 10,244,964 B2
(45) Date of Patent: Apr. 2, 2019

(54) DETECTION OF ACETONE VIA NANOSTRUCTURE SENSORS

(71) Applicant: University of Pittsburgh—Of the Commonwealth System of Higher Education, Pittsburgh, PA (US)

(72) Inventors: Alexander Star, Pittsburgh, PA (US); Mengning Ding, Redondo Beach, CA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 771 days.

(21) Appl. No.: 14/479,316

(22) Filed: Sep. 6, 2014

(65) Prior Publication Data
US 2015/0073290 A1 Mar. 12, 2015

Related U.S. Application Data

(60) Provisional application No. 61/874,538, filed on Sep. 6, 2013.

(51) Int. Cl.
*A61B 5/08* (2006.01)
*A61B 5/145* (2006.01)
*A61B 5/00* (2006.01)

(52) U.S. Cl.
CPC .......... *A61B 5/082* (2013.01); *A61B 5/14532* (2013.01); *A61B 5/7278* (2013.01)

(58) Field of Classification Search
CPC .................................................... A61B 5/082
See application file for complete search history.

(56) References Cited

U.S. PATENT DOCUMENTS

2011/0127446 A1* 6/2011 Star .................. G01N 21/77
250/459.1
2012/0122668 A1* 5/2012 Celiker .................. B01J 21/063
502/242

OTHER PUBLICATIONS

Galessetti et al., Breath Ethanol and Acetone as Indicators of Serum Glucose Levels: An Initial Report, Diabetes Technology and Therapeutics, vol. 7, No. 1, 2005, pp. 115-123.*
Musa-Veloso et al., Breath acetone is a reliable indicator of ketosis in adults consuming ketogenic meals, AM J Clin Nutr 2002;76:65-70.*
Toyooka, T. et al.; A prototype portable breath acetone analyzer for monitoring fat loss; J. Breath Res. 7 (2013), 1-8.
Snow, Eric S. et al.; Capacitance and Conductance of Single-Walled Carbon Nanotubes in the Presence of Chemical Vapors; Nano Lett., vol. 5, No. 12, 2005, 2414-2417.
Righettoni, Marco et al.; Toward Portable Breath Acetone Analysis for Diabetes Detection; J Breath Res. Sep. 2011; 5(3), 1-16.
(Continued)

*Primary Examiner* — Puya Agahi
(74) *Attorney, Agent, or Firm* — Bartony & Associates, LLC

(57) ABSTRACT

A method of detecting at least one of analyte in an environment (such as in breath) includes providing a structure including nanostructures in contact with titanium dioxide, applying electromagnetic radiation to the structure for a period of time, measuring at least one response and using the measured response to determine the presence of the analyte in the environment.

21 Claims, 8 Drawing Sheets

(56) References Cited

OTHER PUBLICATIONS

Guirado-Lopez, Ricardo A. et al.; Interaction of Acetone Molecules with Carbon-Nanotube-Supported TiO2 Nanoparticles:Possible Applications as Room Temperature Molecular Sensitive Coatings; J. Phys. Chem. C 2007, 111, 57-65.
Wang, L. et al.; Nanosensor Device for Breath Acetone Detection, Sensor Lett. 2010, vol. 8, No. 5, 1-4.
Righettoni, Marco et al; Si:WO3 Sensors for Highly Selective Detection of Acetone for Easy Diagnosis of Diabetes by Breath Analysis, Anal. Chem. 2010, 82, 3581-3587.

* cited by examiner

DETECTION OF ACETONE VIA NANOSTRUCTURE SENSORS

CROSS-REFERENCE TO RELATED APPLICATIONS

This application claims benefit of U.S. Provisional Patent Application Ser. No. 61/874,538, filed Sep. 6, 2013, the disclosure of which is incorporated herein by reference.

GOVERNMENTAL INTEREST

This invention was made with government support under grant no.DE-FE0004000 awarded by the National Energy Technology Laboratory of the Department of Energy. The government has certain rights in this invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Diabetes is a chronic lifelong disease caused by a carbohydrate metabolic disorder which has been recognized as one of the greatest causes of death in the developed countries. As a result, there is a high popularity of diabetes monitoring devices in the global market. The market has generated sales of $9.7 billion in the year of 2011, and is estimated to be worth $27.42 billion by 2022.

While currently available diabetes monitoring devices are predominantly based on blood glucose analysis, the development of similar devices utilizing non-invasive, inexpensive and/or easy-to-use breath analysis could change the paradigm of self-diagnosis and self-monitoring of diabetes. Breath acetone was discovered to be a biomarker for diabetes as its concentration increases significantly during periods of glucose deficiency. Acetone concentrations above 1.7 ppm or higher (up to several hundred ppm) could be detected in breath for those who are diabetic, while the breath of healthy human typically contains less than 1 ppm. Therefore, detection of breath acetone has great promise to become an alternative diagnostic or monitoring method for the patients with diabetes. Current clinical breath acetone detection methods are mostly based on gas chromatography (GC) which is expensive and inconvenient.

SUMMARY

In one aspect, a method of detecting at least one analyte in an environment includes providing a structure including nanostructures in contact with titanium dioxide, applying electromagnetic radiation to the structure for a period of time, measuring at least one response (of the structure/nanostructures to gas in the environment) subsequent to applying electromagnetic radiation to the structure for a period of time and using the measured response to determine the presence of the at least one analyte in the environment. In a number of embodiments, the at least one analyte is at least one of ethanol and acetone. A concentration of each of acetone and ethanol may, for example, be determined.

The nanostructures may, for example, include carbon nanostructures. In a number of embodiments, the nanostructures include single walled nanotubes such as single walled carbon nanotubes. In a number of embodiments, the nanostructures are oxidized single-walled carbon nanotubes. The structure may, for example, include a network of oxidized single-walled carbon nanotubes.

In a number of embodiments, the measured response is an electrical property change. A change in at least one electrical property (for example, conductance or resistance) of the nanostructures is measured.

The structure may, for example, include nanostructures which are supported upon a surface. The surface may, for example, include $SiO_2$ or a polymer. The surface may be opaque or translucent.

The titanium dioxide may, for example, be mixed with the nanostructures, immobilized upon the nanostructures, or covalently attached to the nanostructures. In a number of embodiments, the titanium dioxide is covalently attached to the nanostructures.

In a number of embodiments, titanium dioxide is deposited upon the nanostructures via sol-gel synthesis. A precursor may, for example, be first reacted with a functional group upon the surface of the nanostructure and then the precursor may be converted to titanium dioxide. The precursor may, for example, include titanium isopropoxide.

Applying electromagnetic radiation to the structure for a period of time may, for example, include applying UV light or light within the UV spectrum for a period of time (for example, light having wavelengths of 288 nm and 375 nm has been used effectively). In a number of embodiments, a baseline for detection of the at least one analyte is established after application of the electromagnetic/UV energy. In addition to activation of the nanostructure systems hereof, application of electromagnetic/UV energy may also provide a level of control (for example, on/off control) for the operation of sensor systems and methodologies hereof.

In another aspect, a system for detecting at least one analyte includes a structure including nanostructures in contact with titanium dioxide, at least one energy source to apply electromagnetic radiation to the structure for a period of time, and at least one measurement system to measure a response of the nanostructures to a tested environment, wherein the measured response is used to determine the presence of at least one analyte in the tested environment. The nanostructures may, for example, include carbon nanostructures. As described above, the at least one analyte may, for example, be at least one of ethanol and acetone. A concentration of each of acetone and ethanol may, for example, be determined. In a number of embodiments, the nanostructures include single walled nanotubes such as single walled carbon nanotubes. In a number of embodiments, the nanostructures are oxidized single-walled carbon nanotubes. The structure may, for example, include a network of oxidized single-walled carbon nanotubes. The systems may, for example, be used to determine acetone (and, in several embodiments, ethanol) in breath to, for example, determine serum glucose level.

As described above, the measured response may be a measured electrical property change such as a change in conductance or resistance of the nanostructures. The structure may, for example, include nanostructures which are supported upon a surface. The surface may, for example, include $SiO_2$ or a polymer. The surface may be opaque or translucent. As also described above, the titanium dioxide may, for example, be mixed with the nanostructures, immobilized upon the nanostructures, or covalently attached to the nanostructures. In a number of embodiments, the titanium dioxide is covalently attached to the nano structures.

In a number of embodiments, titanium dioxide is deposited upon the nanostructures via sol-gel synthesis. A precursor may, for example, be first reacted with a functional group upon the surface of the nanostructure and then the precursor may be converted to titanium dioxide. The precursor may, for example, include titanium isopropoxide.

In a further aspect, a method of determining glucose level in a subject includes providing a structure including nanostructures in contact with titanium dioxide, applying electromagnetic radiation to the structure for a period of time, placing the structure in fluid connection breath of the subject, measuring at least one response, and using the measured response to determine glucose level in the subject. Acetone concentration may, for example, be determined from the measured response and is used to determine glucose level in the subject. In a number of embodiments, response of the nanostructures to breath of the subject is used to determine acetone concentration and ethanol concentration. The determined acetone concentration and ethanol concentration may then be used to determine glucose level in the subject.

In a further aspect, a method of determining acetone level in a subject includes providing a structure including nanostructures in contact with titanium dioxide, applying electromagnetic radiation to the structure for a period of time, placing the structure in fluid connection breath of the subject, measuring at least one response, and using the measured response to determine acetone level in the subject. Acetone concentration may, for example, be determined from the measured response and be used to determine glucose level in the subject.

Acetone level/concentration can also be used to determine the presence of ketosis, which is a metabolic process in which ketone bodies (acetone, acetoacetic acid, and β-hydroxybutyric acid) supply the bulk of the body's energy demands. The average person's metabolic process is glycolysis, wherein glucose (as opposed to ketone bodies) is the primary supply of transportable energy. A person undergoes ketosis, for example, if he or she is on a ketogenic diet (a popular alternative treatment for juvenile epilepsy), has recently exercised, or is in a state of starvation. Monitoring ketosis is important for healthcare providers in determining the efficacy of a ketogenic diet or the degree of starvation. Monitoring ketosis may also be important for weight watchers and athletes. Currently, the two methods to monitor ketosis are blood sampling and nitroprusside-based urinary dipsticks. Urinary dipsticks are non-invasive, but are only semi-quantitative and do not reliably represent blood ketone values. Blood sampling is highly quantitative, but invasive. Acetone sensing, as described herein, is non-invasive and has shown high correlation with blood ketone concentration.

Application of electromagnetic energy such as UV energy to a structure including nanostructures and titanium dioxide before the structure is exposed to a gas sample from an environment to be tested has been found to substantially improve lower limits of detection of an analyte such as acetone.

The present devices, systems, and methods, along with the attributes and attendant advantages thereof, will best be appreciated and understood in view of the following detailed description taken in conjunction with the accompanying drawings.

DETAILED DESCRIPTION

Figure 1:
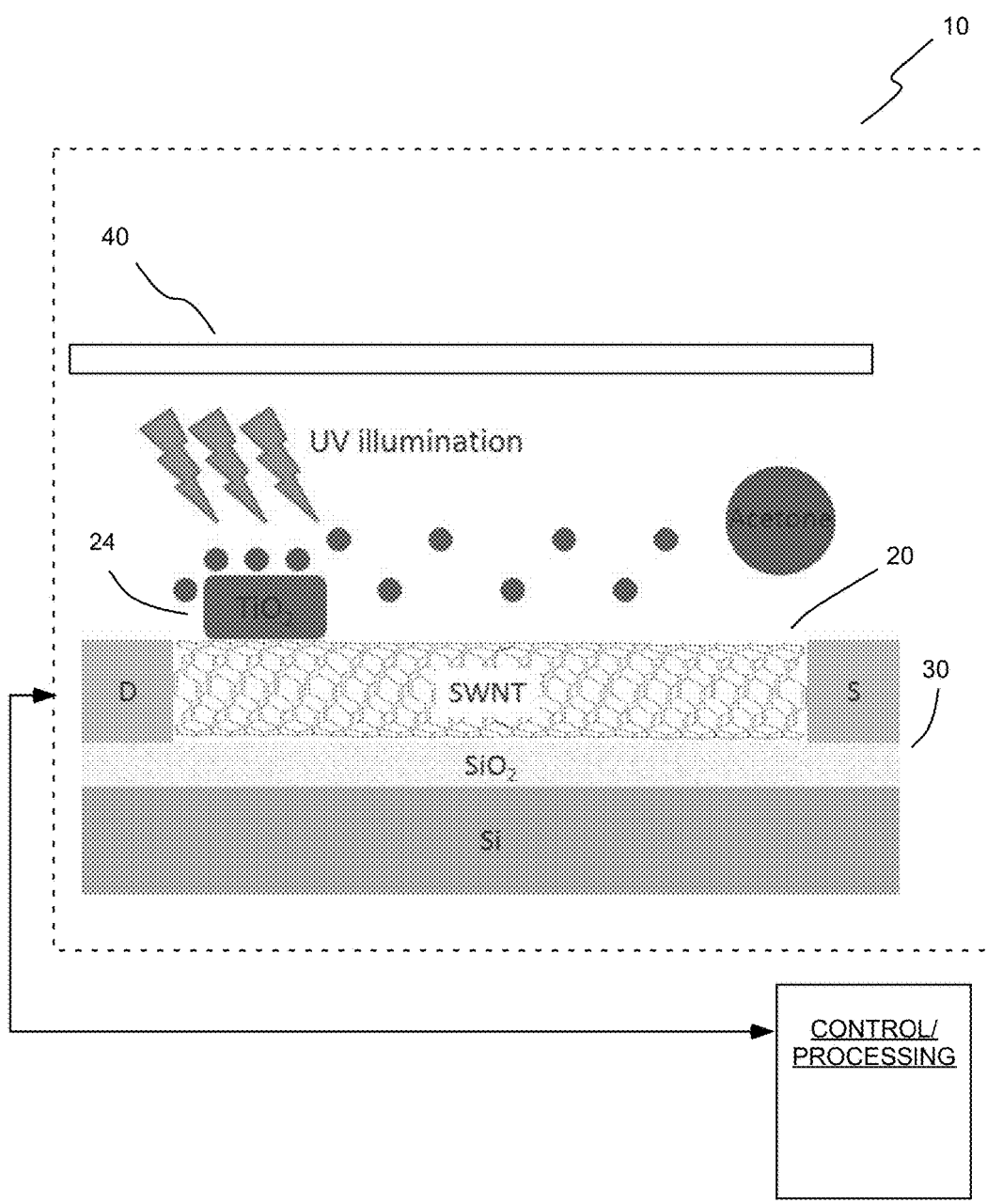
FIG. 1 illustrates a schematic representation of electrical detection of acetone using single-walled carbon nanotube-titanium dioxide nanohybrids (SWNT-$TiO_2$).

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a nanostructure" includes a plurality of such nanostructure and equivalents thereof known to those skilled in the art, and so forth, and reference to "the nanostructure" is a reference to one or more such nanostructures and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

Compared to current clinical breath acetone detection methods (predominantly based on gas chromatography), nanostructure-based (for example, carbon nanotube-(CNT-based)) solid-state chemiresistive sensors offer many advantages. For example, nanostructure-based such as CNT-based sensors are portable, user-friendly, low-cost (¢ per unit), low power consumption (room temperature, low voltage operation) and CMOS compatible (for example, for further incorporation into multiple electronic devices). These advantages may provide an ideal solution for the market needs of, for example, non-invasive self-diagnostic and self-monitoring devices for diabetes via breath analysis.

We have demonstrated a number of strategies to functionalize electrically conductive nanostructures such as single-walled carbon nanotubes (SWNTs) with titanium dioxide ($TiO_2$) nanostructures for the development of, for example, acetone sensors. Various other nanostructures are suitable for use herein. Such nanostructures include, for example, multi-walled nanotubes, nanowires, nanofibers, nanorods, nanospheres, or the like, or mixtures of such nanostructures. Moreover, in addition to carbon, those skilled in the art will appreciate that the nanostructures hereof can be formed of boron, boron nitride, and carbon boron nitride, silicon, germanium, gallium nitride, zinc oxide, indium phosphide, molybdenum disulphide, silver, and/or other suitable materials.

A semiconducting SWNT or network of SWNTs 20 (or other nanostructures) can, for example, be disposed upon a substrate 30 (for example, $SiO_2$) and contacted by two conductive (for example, metallic such as Au and/or Ti) electrodes representing a source (S) and a drain (D). In a number of embodiments, $TiO_2$ layer 24 is be provided in connection with the SWNT network 20.

In single-walled carbon nanotubes, all carbon atoms are located on the surface where current flows, making a stable conduction channel that is extremely sensitive to a surrounding chemical environment. Nanotubes, including SWNT's, have the ability to change conductance in response to interaction with (for example, absorption of) different gases. This characteristic is, for example, implemented in system 10. In the embodiment illustrated, electromagnetic energy (for example, UV light) is transmitted from an energy source 40 from above. Energy can additionally or alternatively be transmitted through an optically transparent support (for example, an optically transparent quartz support) from below.

Measurements made with devices or systems including random networks of SWNTs can be advantageous because random network devices are less prone to failure as a result of the large number of conduction pathways. Additionally, while random network devices may not provide information on individual nanotube response, as with singly isolated SWNTs, they possess an intrinsic averaging effect in that they remove nanotube-to-nanotube variation as a result of the combined response of the entire network. As an analyte comes into contact with the device surface, SWNT conductance is modified to produce a detection signal.

In the SWNT-$TiO_2$ hybrid structure of FIG. 1, SWNTs were used as electrical signal transducer and $TiO_2$ was used as an acetone recognition layer. In a number of embodiments, $TiO_2$ functionalization of SWNTs was carried out in solution phase, and the SWNT-$TiO_2$ hybrids were drop-casted onto a $SiO_2$ film grown on a Si wafer with interdigitated gold electrodes. For gas detection, the devices in a number of studies were first activated by a low-intensity ultraviolet (UV) light (365 nm in wavelength, 25 $\mu W.cm^{-2}$), and the electrical conductivity (or resistivity) of functionalized SWNTs was measured using programmable digital sourcemeter under a direct voltage supply. After activation by illumination with ultraviolet light, interactions between $TiO_2$ and acetone was found to cause a significant change in the electrical conductivity of SWNT and enabled acetone detection. Without limitation to any mechanism, upon exposure to acetone, the conductivity of the SWNT-$TiO_2$ changes as a result of the electronic interactions between SWNT and $TiO_2$, originated from the adsorption of acetone molecules on the $TiO_2$ surface and subsequent charge transfer. The change in device conductivity is proportional to acetone concentration. The energy-/photo-induced sensitivity of nanostructures functionalized with $TiO_2$ provides a significant improvement in sensitivity as compared to functionalized nanostructures that have not been activated/sensitized via application of energy.

Figure 2A:
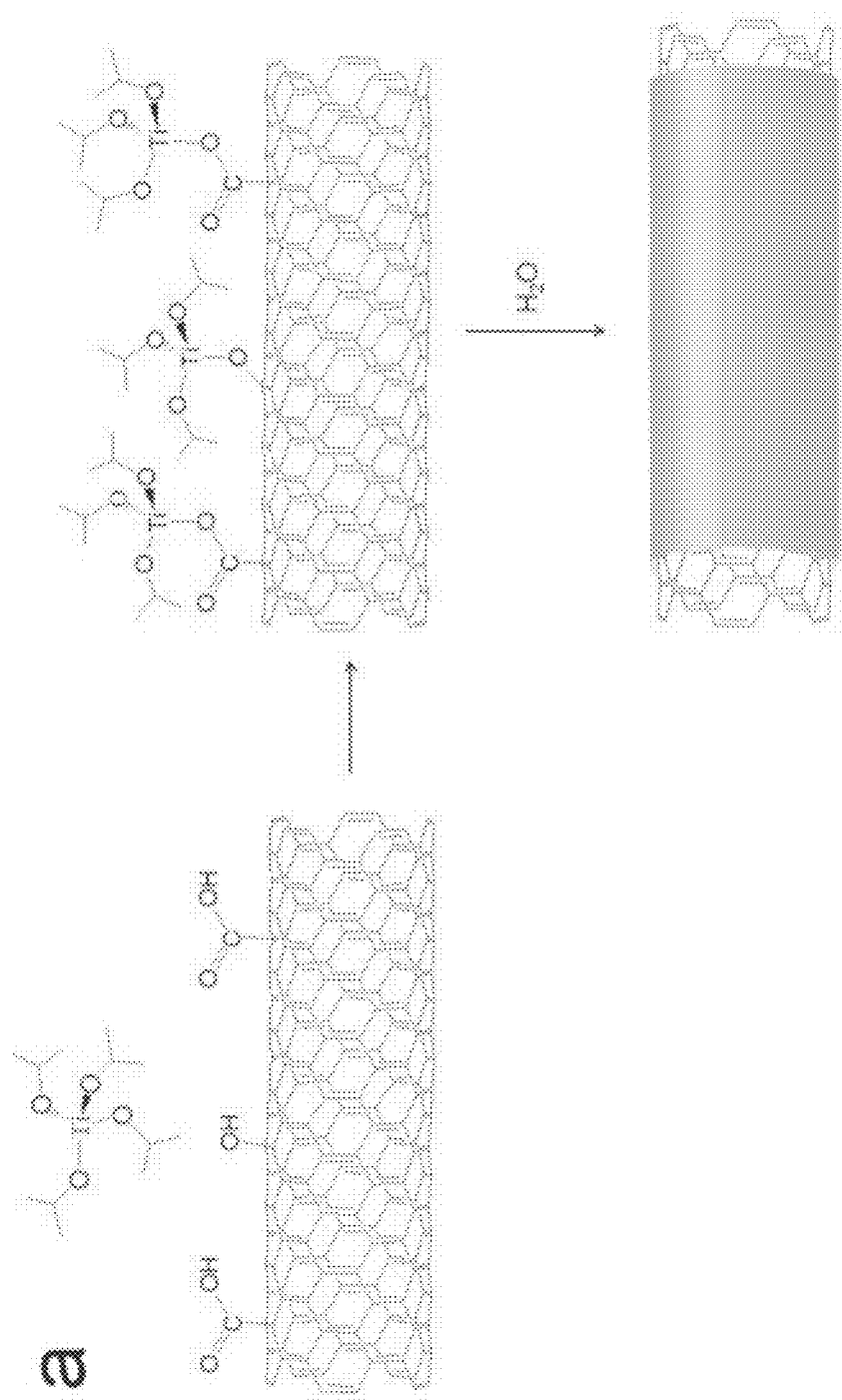
FIG. 2A illustrates an embodiment of a sol-gel synthesis of SWNT@$TiO_2$ hybrid using titanium isopropoxide, Ti(OiPr)$_4$ as a precursor and oxidized SWNTs as a template, wherein the Ti(OiPr)$_4$ precursor first reacted with oxygen surface functionalities of SWNTs, and further hydrolysis upon addition of water resulted in the growth of a $TiO_2$ shell over SWNTs.
Figure 2B:
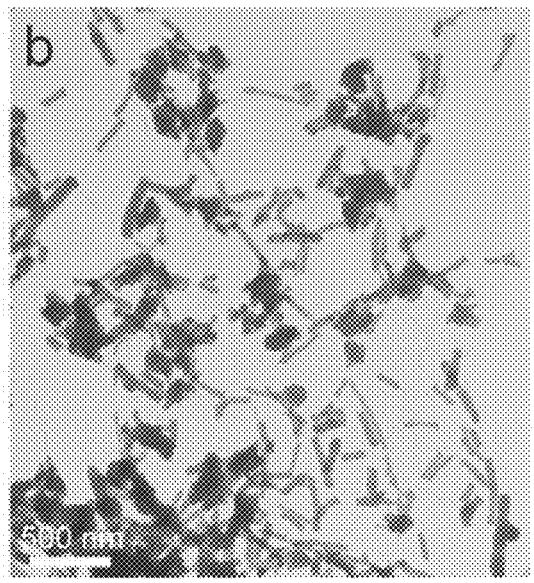
FIG. 2B illustrates a transmission electron microscopy (TEM) image showing the formation of pseudo one-dimensional $TiO_2$ shells over SWNTs.
Figure 2C:
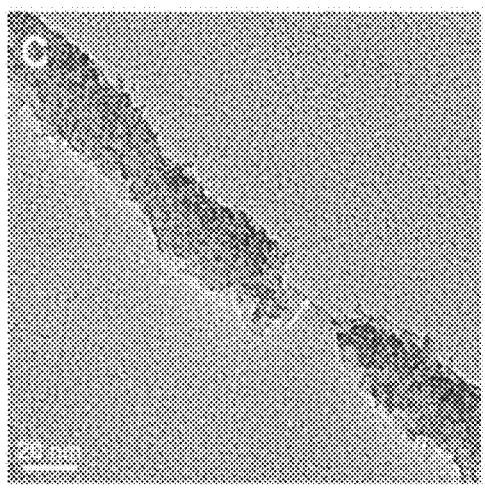
FIG. 2C illustrates another transmission electron microscopy image showing the formation of pseudo one-dimensional $TiO_2$ shells over SWNTs, wherein an arrow indicates an uncoated SWNT segment.
Figure 2D:
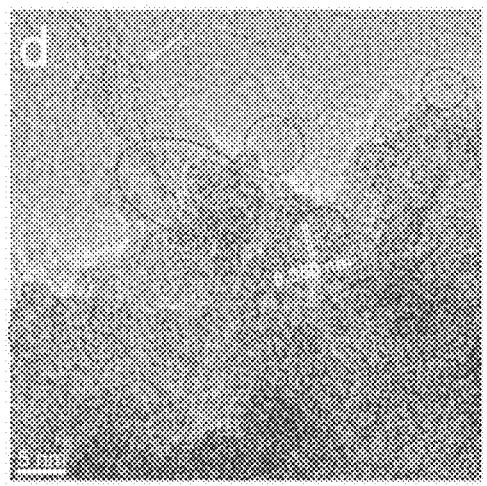
FIG. 2D illustrates a high-resolution TEM image of the SWNT-$TiO_2$ boundary, with small crystalline regions highlighted by ovals, while arrows indicate uncoated SWNT segments.
Figure 2E:
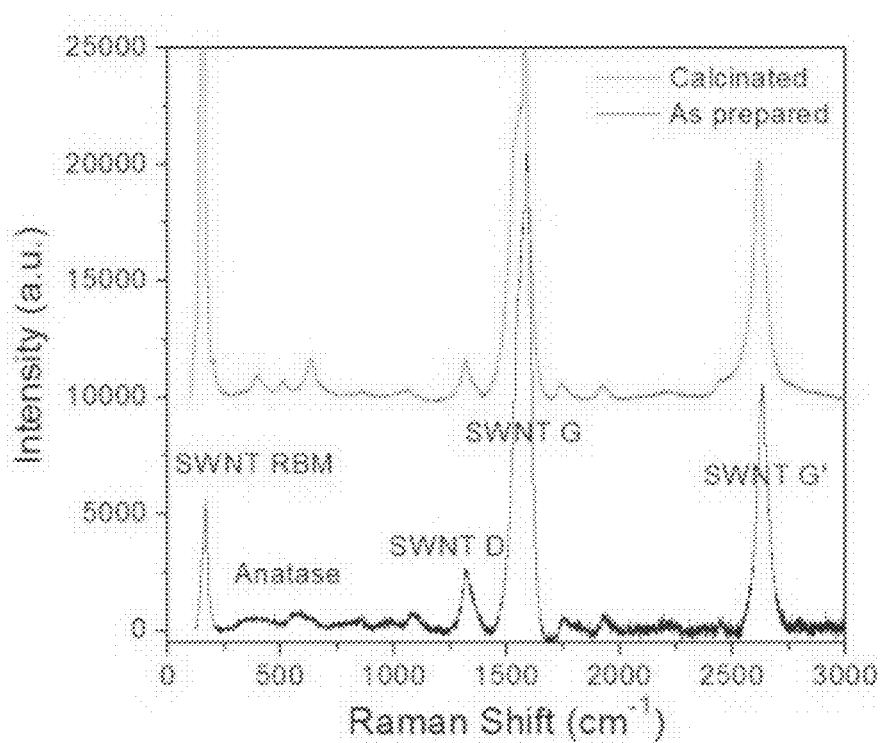
FIG. 2E illustrates Raman spectroscopy results for the SWNT@$TiO_2$ hybrids before and after calcination.

In several representative embodiments, an SWNT@$TiO_2$ core/shell nanohybrid structure was used. The growth of a $TiO_2$ layer over individual SWNT was achieved through a two-step sol-gel synthesis approach, as illustrated in FIG. 2A. Carboxyl or hydroxyl groups on the surface of SWNTs first reacted with titanium(IV) isopropoxide (Ti(OiPr)$_4$), which was used as the $TiO_2$ precursor. The grafted —O—Ti (OiPr)$_3$ underwent further hydrolysis and condensation steps upon addition of water. The sol-gel process initiated from the surface of SWNTs produced a one-dimensional core/shell structure. Transmission electron microscopy (TEM) images (FIGS. 2B, 2C and 2D) illustrated the morphology of this o-SWNT@$TiO_2$ core/shell hybrid material. The major part of as-synthesized $TiO_2$ appeared to be amorphous, with small crystalline regions observed in high-resolution TEM (HR-TEM) images (see FIG. 2D). The interfringe distances of the crystal lattice in these areas were determined to be 0.350 nm, which correspond to the lattice spacing of anatase (101) surface. Similar to other $TiO_2$ materials prepared by a sol-gel approach, the overall crystallinity of the SWNT/$TiO_2$ nanohybrids could be tuned upon further calcinations, as evidenced by Raman spectroscopy (see FIG. 2E).

Figures 3A, 3B, 3C:
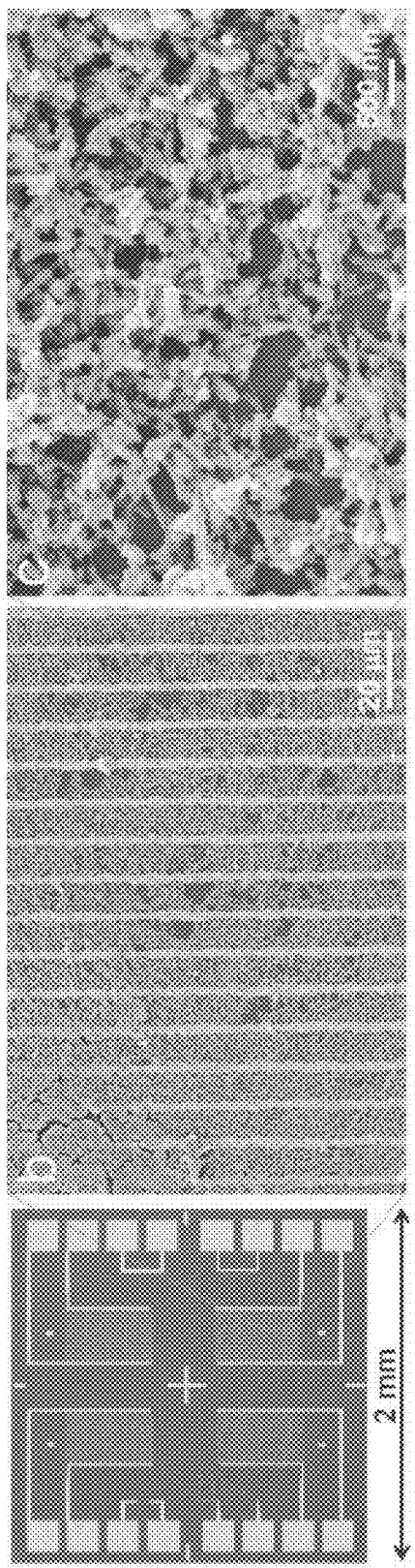
FIG. 3A illustrates an optical image of a silicon chip with four sets of interdigitated gold electrodes used in studies hereof.
FIG. 3B illustrates an SEM image of the SWNT@$TiO_2$ core/shell hybrid film deposited between the gold electrodes.
FIG. 3C illustrates an enlarged SEM image of the SWNT@$TiO_2$ core/shell hybrid film deposited between the gold electrodes.
Figure 3D:
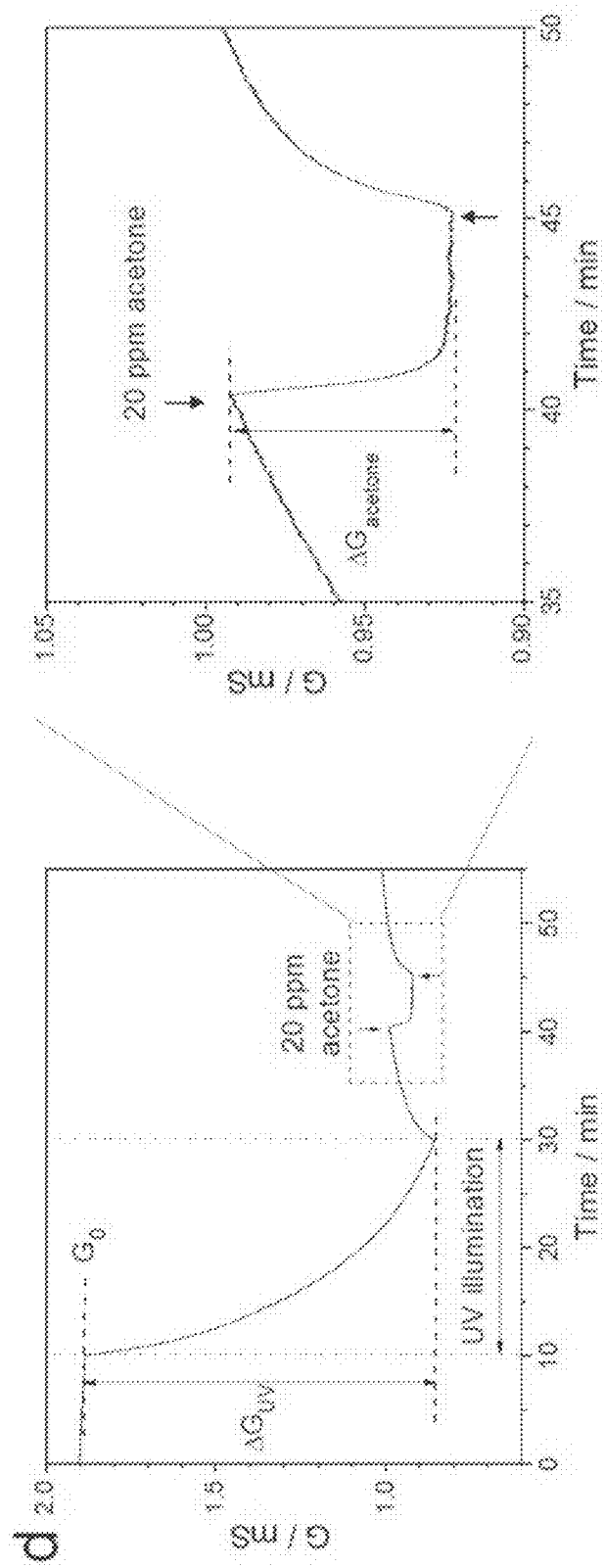
FIG. 3D illustrates two graphs of conductance (G) versus time showing the response to ultraviolet light (365 nm) illumination and acetone vapors (20 ppm, balanced in $N_2$), wherein arrows indicate the beginning and end of acetone exposure, and wherein the graph on the right sets forth an enlarged view of the indicated portion of the graph on the left.

In a number of studies, a conductive film was fabricated via deposition of SWNT@$TiO_2$ hybrid on a Si wafer with $SiO_2$ insulating layer and interdigitated gold electrodes (10 μm pitch) prepared by standard photolithography (See FIGS. 3A through 3C). FIGS. 3B and 3C illustrate scanning electron microscopy (SEM) images of o-SWNT@$TiO_2$ hybrid network forming electrical connections between the gold electrodes. Upon illumination with ultraviolet light (365 nm), SWNT@$TiO_2$ hybrid networks showed a decrease in conductance, as demonstrated in FIG. 3D. When the UV light was turned off, the slowly recovering conductance of SWNT@$TiO_2$ went close to a steady state after 10 min in $N_2$ and set up a new baseline that could be utilized for chemical detection. As shown in FIG. 3D, exposure to 20 ppm acetone vapors led to a fast decrease in the conductance of o-SWNT@$TiO_2$ device, with complete recovery to the baseline when acetone vapor exposure was terminated.

Figures 3E, 3F:
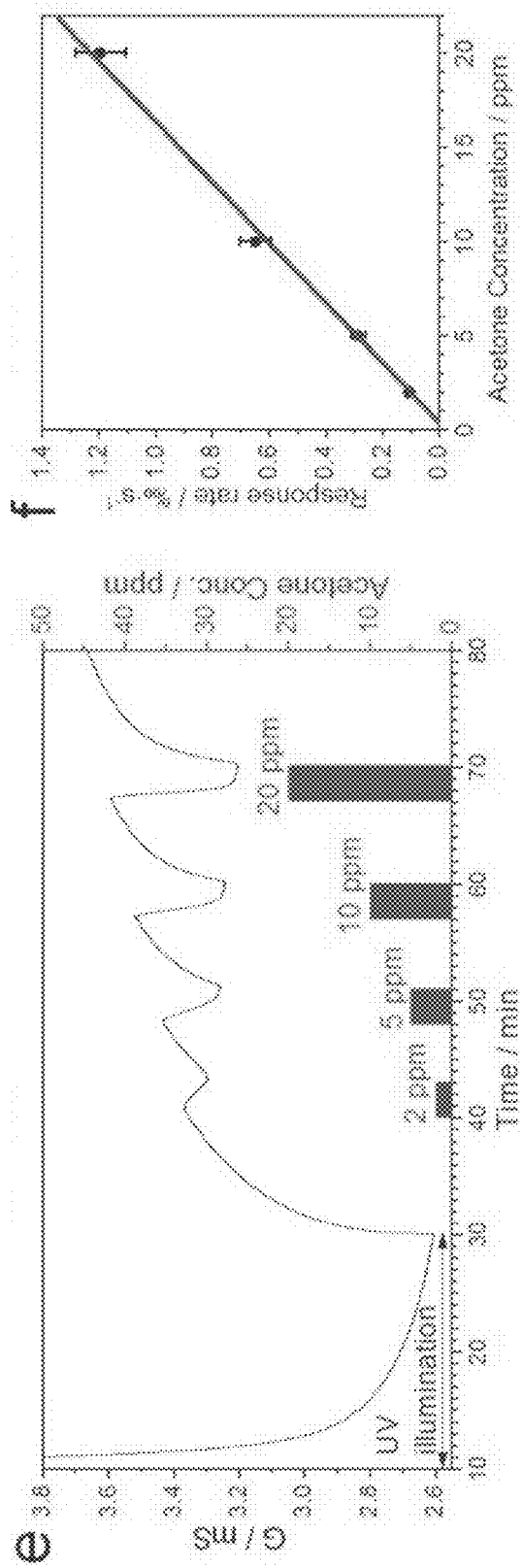
FIG. 3E illustrates the conductance (G) response of a studied device hereof to acetone vapors of varying concentrations (balanced in $N_2$) after UV illumination.
FIG. 3F illustrates acetone response rate (that is, relative conductance change per unit time) of SWNT@$TiO_2$ devices (n=10).

Multiple acetone concentrations were measured in a number of studies, and different response rates were observed to the varying concentrations of acetone vapors, as demonstrated in FIG. 3E. A linear relationship between the electrical response rate at the first 60 seconds (fast response region) and the acetone concentrations was discovered, which could serve as calibration curve for the sensor (see FIG. 3F). For 180 seconds of exposure time, we calculated a signal to noise ratio (S/N) of 14 for 2 ppm of acetone, and a detection limit of 0.4 ppm was determined (using S/N=3) for the studied SWNT@$TiO_2$ acetone sensors. This detection limit is much lower than previously reported SWNT-based detection systems for acetone. Cross-sensitivity tests to major components of human breath ($O_2$, $CO_2$, $H_2O$ and ethanol) were also performed. Negligible $CO_2$ response of SWNT@$TiO_2$ was observed, and SWNT@$TiO_2$ sensor could still successfully detect 20 ppm of acetone vapors in both air and high humidity backgrounds. As a result of different response dynamics, electrical response of SWNT@$TiO_2$ to acetone and ethanol vapors can be distinguished via their response rates. Thus, the sensor hereof may also be used to detect ethanol. In a number of embodiments, the concentration of acetone and ethanol may be correlated to serum (blood) glucose levels. Without limitation to any mechanism, ethanol is produced as a result of alcoholic fermentation of glucose by gut bacteria and yeast, while acetone is formed from oxidations of free fatty acids, influenced by glucose metabolism.

In a number of other representative examples SWNTs were simply mechanically mixed with $TiO_2$ powders. In that regard, SWNT-$TiO_2$ nanohybrid sensor materials could also be fabricated by mechanically mixing commercial pristine or oxidized SWNTs and commercial Anatase or Rutile $TiO_2$ nanopowders using, for example, sonication.

In still other representative embodiments, SWNTs were covalently bonded with $TiO_2$ powders. In that regard, SWNT-$TiO_2$ nanohybrid sensor materials could be fabricated by covalently attaching commercially available Anatase or Rutile $TiO_2$ nanopowders to oxidized SWNTs. In a number of embodiments, Ti(OiPr)$_4$ was first added to react with oxidized SWNTs, then suspension of $TiO_2$ nanopowders was added to graft to the organic liker. Acetone sensitivities of the studied SWNT-$TiO_2$ hybrid systems of different morphologies and interface conditions are summarized in FIG. 4. Commercially available pristine or oxidized SWNTs and, for example, Anatase $TiO_2$(A) samples were mixed by either mechanical mixing (using sonication) or covalent attachment (see methods for details). Similar electrical measurements were performed on all these SWNT-$TiO_2$ hybrid systems and their UV and acetone responses are summarized in FIG. 4.

Figure 4:
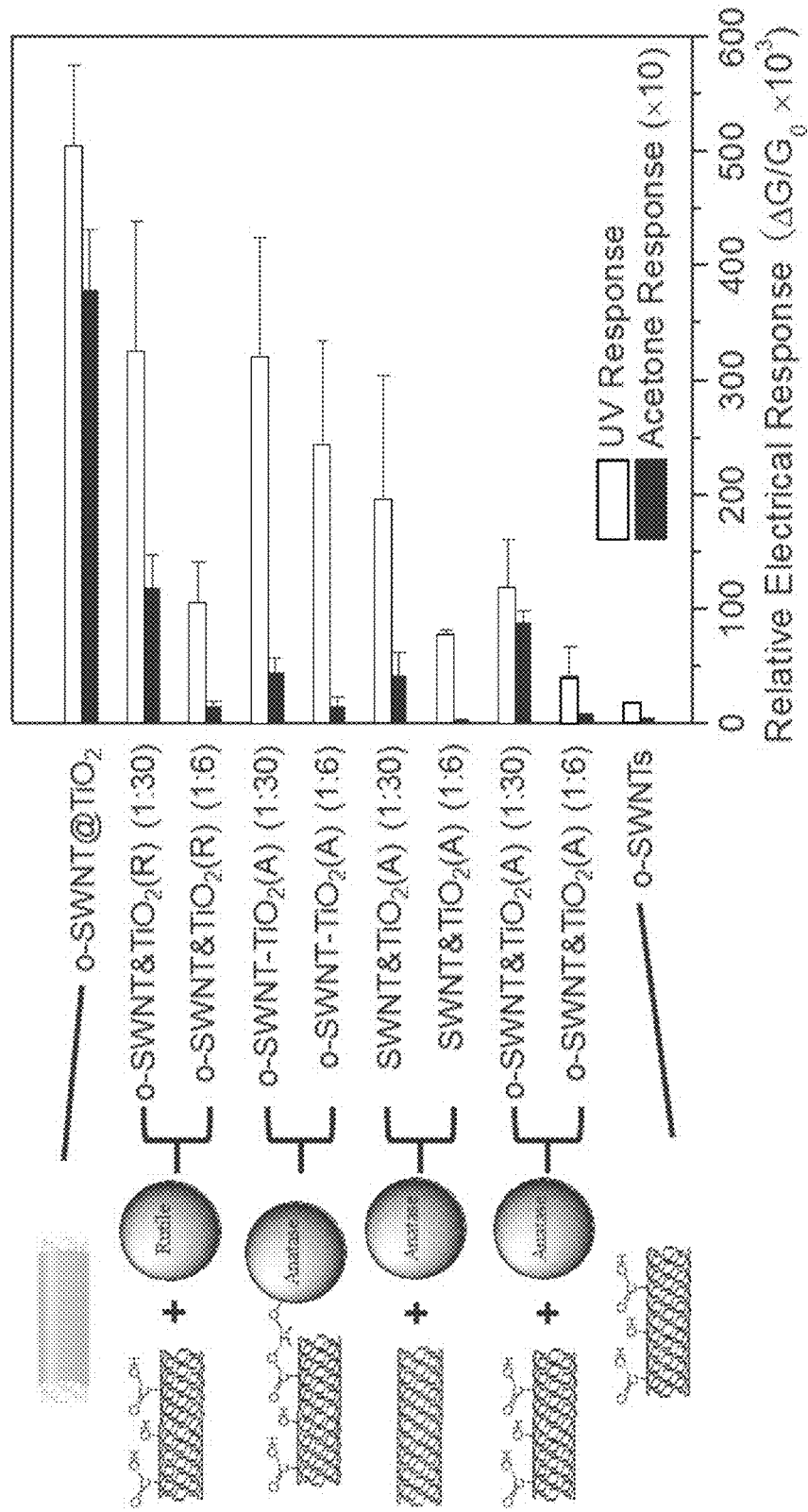
FIG. 4 illustrates a schematic illustrations (left) of different SWNT-$TiO_2$ hybrid systems including: oxidized SWNTs (o-SWNTs), as-prepared o-SWNT@$TiO_2$ core/shell hybrid, covalently linked anatase nanopowders with o-SWNTs (o-SWNT-$TiO_2$(A)), mechanically mixed pristine SWNTs and anatase nanopowders (SWNT&$TiO_2$(A)), mechanically mixed o-SWNTs and anatase nanopowders (o-SWNT&$TiO_2$(A)), and mechanically mixed o-SWNTs and rutile nanopowders (o-SWNT&$TiO_2$(R)), wherein the numbers after each label indicate the weight ratio of SWNTs to $TiO_2$ in the hybrid, and wherein the right panel illustrates the UV (white bars) and acetone responses (black bars) of each hybrid system, with standard deviation (n=15; for comparison, acetone responses were multiplied by a factor of ten).

As illustrated in FIG. 4, addition of $TiO_2$ dramatically increased the UV response of the studied devices compared with bare SWNTs network (either pristine or oxidized SWNTs), and larger UV responses were observed for a higher amount of $TiO_2$ in all hybrid systems, regardless of their interconnections with SWNTs. Without limitation to any mechanism, such difference in the magnitude of conductance change and its correlation with the $TiO_2$ loading indicated that the electrical behavior of SWNT-$TiO_2$ hybrid systems is a result of the interfacial charge transfer process. While pristine SWNTs and oxidized SWNTs showed similar UV and acetone sensitivities when mechanically mixed with anatase $TiO_2$(A) nanocrystals, covalent attachment between $TiO_2$ nanocrystals and SWNTs led to a significant increase in the UV response (o-SWNT-$TiO_2$(A) vs. o-SWNT&$TiO_2$ (A) in FIG. 4). This difference indicates that covalent linkage between $TiO_2$ and SWNTs led to enhanced electron transfer efficiency and therefore a better charge-hole separation in the hybrid system, while the type of SWNTs (pristine vs. oxidized) had less influence. Overall, o-SWNT@$TiO_2$ presented the largest UV response. We can conclude from all these results that this hybrid system presents an efficient electronic transfer at interface upon UV irradiation.

As also illustrated in FIG. 4, increasing the amount of $TiO_2$ resulted in enhanced acetone sensitivity in all studied nanohybrid systems, which confirmed its role of recognition layer. As set forth above, compared with other hybrid systems, o-SWNT@$TiO_2$ core/shell hybrid demonstrated the highest acetone sensitivity. Without limitation to any mechanism, this result may arise from the following factors: i) the abundant covalent bonding between SWNTs and $TiO_2$ facilitates the electronic coupling and interactions across the hybrid interface, leading to a more efficient and sensitive interfacial charge transfer (as also indicated by its best UV response); and ii) the less ordered structure of as-synthesized $TiO_2$ (amorphous in nature with few small crystalline areas) offers more oxygen vacancies or unsaturated surface Ti centers that were more reactive to acetone molecules, as compared to the highly crystalized commercial $TiO_2$ nanoparticles (FIG. 4).

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:
1. A method of detecting at least one analyte selected from the group of acetone and ethanol in an environment, comprising:
providing a structure comprising nanostructures in contact with titanium dioxide positioned between two conductive electrodes;

applying electromagnetic radiation to the structure for a period of time;

measuring at least one response comprising a change in conductivity or resistivity of the structure via the two conductive electrodes upon exposure to the environment subsequent to applying electromagnetic radiation to the structure for the period of time; and determining the presence of the at least one analyte selected from the group of acetone and ethanol in the environment from the measured response.

2. The method of claim 1 wherein the at least one analyte is ethanol.

3. The method of claim 1 wherein the at least one analyte is acetone.

4. The method of claim 3 wherein the nanostructures comprise carbon nanostructures.

5. The method of claim 4 wherein the structure comprises a network of oxidized single-walled carbon nanotubes.

6. The method of claim 3 wherein the measured response is an electrical property change.

7. The method of claim 3 wherein the structure comprises nanostructures which are supported upon a surface.

8. The method of claim 7 wherein the surface comprises $SiO_2$ or a polymer.

9. The method of claim 4 wherein the titanium dioxide is mixed with the nanostructures, immobilized upon the nanostructures, or covalently attached to the nanostructures.

10. The method of claim 9 wherein the titanium dioxide is covalently attached to the nanostructures.

11. The method of claim 10 wherein the nanostructures are oxidized single-walled carbon nanotubes.

12. The method of claim 1 wherein applying electromagnetic radiation to the structure for the period of time comprises applying UV light for the period of time and a baseline for detection of the at least one analyte is established after application of the UV light.

13. The method of claim 9 wherein titanium dioxide is deposited upon the nanostructures via sol-gel synthesis.

14. A system for detecting at least one analyte selected from the group of acetone and ethanol, comprising:
 a first electrode;
 a second electrode, spaced from the first electrode;
 a structure comprising nanostructures in contact with titanium dioxide positioned between the first electrode and the second electrode;
 at least one energy source to apply electromagnetic radiation to the structure for a period of time; and
 at least one measurement system in operative connection with the first electrode and the second electrode to measure a response comprising a change in conductivity or resistivity, the measured response determining a presence of the at least one analyte selected from the group of acetone and ethanol in an environment.

15. The system of claim 14 wherein the nanostructures comprise carbon nanostructures.

16. The system f claim 14 wherein the titanium dioxide is mixed with the nanostructures, immobilized upon the nanostructures, or covalently attached to the nanostructures.

17. A method of determining an acetone level in a subject, comprising:
 providing a structure comprising nanostructures in contact with titanium dioxide, the structure being positioned between a first electrode and a second electrode;
 applying electromagnetic radiation to the structure for a period of time;
 placing the structure in fluid connection with breath of the subject;
 measuring at least one response comprising a change in conductivity or resistivity; and
 determining an acetone level in the subject from the measured response.

18. The method of claim 17 wherein at least a concentration of acetone is determined from the measured response and is used to determine a glucose level in the subject.

19. The method of claim 18 wherein the measured response of the nanostructures to breath of the subject is also used to determine a concentration of ethanol, and acetone concentration and ethanol concentration are used to determine the glucose level in the subject.

20. The method of claim 18 wherein the nanostructures comprise carbon nanostructures and the titanium dioxide is covalently attached to the nanostructures.

21. The method of claim 18 wherein a concentration of at least acetone is determined from the measured response and is used to determine a presence of ketosis.

* * * * *

UNITED STATES PATENT AND TRADEMARK OFFICE
CERTIFICATE OF CORRECTION

PATENT NO. : 10,244,964 B2
APPLICATION NO. : 14/479316
DATED : April 2, 2019
INVENTOR(S) : Alexander Star and Mengning Ding It is certified that error appears in the above-identified patent and that said Letters Patent is hereby corrected as shown below:

In the Claims

Column 10, Claim 16, Line 14, delete "The system f claim 14" and insert --The system of claim 14--

Signed and Sealed this
Sixteenth Day of July, 2019

Andrei Iancu
*Director of the United States Patent and Trademark Office*